(12) United States Patent
Merlen et al.

(10) Patent No.: US 6,486,372 B1
(45) Date of Patent: Nov. 26, 2002

(54) CATALYST BASED ON DEALUMINATED MORDENITE CONTAINING AT LEAST ONE METAL FROM GROUPS VI, VII OR VIII, AND ITS USE FOR DISMUTATION AND/OR TRANSALKYLATION OF AROMATIC HYDROCARBONS

(75) Inventors: Elisabeth Merlen, Rueil Malmaison; Fabio Alario, Neuilly sur Seine, both of (FR)

(73) Assignee: Institut Francais du Petrole, Malmaison Cedex (FR)

( * ) Notice: Subject to any disclaimer, the term of this patent is extended or adjusted under 35 U.S.C. 154(b) by 0 days.

(21) Appl. No.: 09/056,741

(22) Filed: Apr. 8, 1998

(30) Foreign Application Priority Data

Apr. 9, 1997 (FR) .............................. 97/04451

(51) Int. Cl.$^7$ ................................. C07C 2/68
(52) U.S. Cl. .................. 585/467; 585/475; 502/64; 502/66; 502/74; 502/78
(58) Field of Search .............. 502/64, 66, 74, 502/78; 585/467, 475

(56) References Cited

U.S. PATENT DOCUMENTS 3,480,539 A * 11/1969 Voorhies, Jr. et al. ........ 502/78
3,849,340 A * 11/1974 Pollitzer ...................... 502/78
4,501,656 A * 2/1985 Dufresne et al. ............ 208/111
4,665,272 A   5/1987 Bakas et al. ................ 585/739
4,723,048 A * 2/1988 Dufresne et al. ............ 585/474
4,943,546 A * 7/1990 Travers et al. ................ 502/66
4,977,121 A * 12/1990 Dufresne et al. ............. 502/66

FOREIGN PATENT DOCUMENTS

| EP | 0 308 302 | 3/1989 |
| EP | 0 573 347 | 12/1993 |
| FR | 2 084 704 | 12/1971 |

* cited by examiner

Primary Examiner—Stanley S. Silverman
Assistant Examiner—Christina Ildebrando
(74) Attorney, Agent, or Firm—Millen, White, Zelano & Branigan, P.C.

(57) ABSTRACT

A catalyst for transforming aromatic hydrocarbons, preferably for dismutation of toluene to produce benzene and xylenes and transalkylation of toluene and aromatic compounds containing at least 9 carbon atoms per molecule to produce xylenes, contains 40% to 90% by weight of a mordenite in its acid form in a proportion of and 10% to 60% by weight of binders. The mordenite comprises less than 0.1% by weight of sodium and has a $SiO_2/A_2O_3$ molar ratio of over 70. The catalyst also contains at least one metal from groups VI, VII or VIII and optionally an additional metal from groups III or IV.

22 Claims, No Drawings

CATALYST BASED ON DEALUMINATED MORDENITE CONTAINING AT LEAST ONE METAL FROM GROUPS VI, VII OR VIII, AND ITS USE FOR DISMUTATION AND/OR TRANSALKYLATION OF AROMATIC HYDROCARBONS

FIELD OF THE INVENTION

The present invention relates to a catalyst for transforming aromatic hydrocarbons. More precisely, it relates to a catalyst for dismutation of toluene to produce benzene and xylenes, and transalkylation of alkylaromatic hydrocarbons, preferably transalkylation of toluene and aromatic compounds containing at least 9 carbon atoms per molecule, preferably trimethylbenzenes, to produce xylenes.

SUMMARY OF THE INVENTION

The catalyst of the present invention contains a mordenite with a high silicon content and in a large proportion with respect to a binder. At least part of this mordenite is present in its acid form, generally in a proportion of 40% to 90% by weight, preferably 75% to 85% by weight, and the binder, preferably alumina, is generally present in a proportion of 10% to 60% by weight, preferably 15% to 25% by weight. The mordenite contains less than 0.1% by weight, preferably less then 0.05% by weight, of sodium, and has an $SiO_2/A_2O_3$ molar ratio of over 70, preferably in the range 80 to 120. The catalyst also contains at least one metal from the group formed by elements from groups VI, VII and VUI of the periodic table, preferably palladium, platinum, rhenium and/or nickel, more preferably platinum and/or nickel, and most preferably nickel, in an amount, expressed with respect to the mordenite, in the range 0.01% to 5% by weight, preferably in the range 0.1% to 3% by weight. Finally, the catalyst optionally additionally contains at least one metal from the group formed by elements from groups III and IV of the periodic table in an amount, expressed with respect to the mordenite, which is in the range 0.01% to 5%, preferably 0.1% to 3% by weight. The present invention also concerns the use of the catalyst for dismutation and/or transalkylation of alkylaromatic hydrocarbons.

BACKGROUND OF THE INVENTION

A number of dismutation and transalkylation catalysts have already been described in the prior art, some being based on mordenite and metals. U.S. Pat. No. 3,281,483 mentions mordenites exchanged essentially with silver or nickel ions and U.S. Pat. No. 3,780,121 describes a mordenite exchanged with metals from group IB of the periodic table characterized by an $SiO_2/Al_2O_3$ molar ratio in the range 12 to 80. Further, U.S. Pat. No. 3,629,351 also describes a mordenite containing ions of metals from groups IB, VA, VIA, IIA and VIII of the periodic table.

More recently, Japanese patent JP-A-63301834 describes a catalyst comprising a mordenite comprising a metal which can, inter alia, be nickel and can be introduced during synthesis of the zeolite. In U.S. Pat. Nos. 4,151,120, 41,180, 693 and 4,210,770, the catalyst comprises mordenite with a $SiO_2/Al_2O_3$ ratio in the range 10 to 100 and at least one metal selected from the group formed by Ni, Co, Ag and Pd, the mordenite undergoing at least one calcining treatment in the presence of steam. Finally, in U.S. Pat. No. 5,475,180, the Ni on mordenite catalyst is modified in the presence of a heavy reformate.

DETAILED DESCRIPTION

We have discovered that, surprisingly, a catalyst for transforming aromatic hydrocarbons containing a mordenite zeolite with an $SiO_2/Al_2O_3$ molar ratio of over 70, preferably in the range 80 to 120, and at least one metal from the group formed by elements from groups VI, VII and VIII, preferably palladium, platinum, rhenium and/or nickel, more preferably platinum and/or nickel, and most preferably nickel, in an amount, expressed with respect to the mordenite, in the range 0.01% to 5% by weight, preferably 0.1% to 3% by weight, the catalyst also optionally comprising at least one metal from the group formed by elements from groups III and IV, results in substantially improved performances, principally in terms of toluene conversion and stability over time, over the catalysts described in U.S. Pat. Nos. 4,151,120, 41,180,693 and 4,210,770 where the catalyst comprises mordenite in an $SiO_2/Al_2O_3$ ratio in the range 10 to 100 and at least one metal selected from the group formed by Ni, Co, Ag and Pd, for the dismutation of toluene to produce benzene and xylenes, and for the transalkylation of toluene and AC9(+) compounds to produce xylenes.

The present invention concerns a catalyst for dismutation and/or transalkylation of toluene and/or alkylaromatic compounds containing at least 9 carbon atoms per molecule which contains:

40% to 90% by weight, preferably 75% to 85% by weight, of at least one zeolite with a mordenite structure which is at least partially in its acid form, characterized in that its Si/Al molar ratio is over 35, preferably in the range 40 to 60, said mordenite containing at most 0.1% by weight (expressed with respect to zeolite) of sodium, preferably at most 0.05% by weight of sodium;

0.01% to 5%, preferably 0.1% to 3% by weight, with respect to the zeolite, of at least one metal from the group formed by elements from groups VI, VII and VIII of the periodic table, i.e., selected from the group formed by chromium, molybdenum, tungsten, manganese, technetium, rhenium, iron, ruthenium, osmium, cobalt, rhodium, iridium, nickel, palladium and platinum, preferably selected from the group formed by platinum, palladium, rhenium and nickel, preferably again platinum or nickel and most preferably nickel;

10% to 60% by weight, preferably 15% to 25% by weight, of at least one binder, preferably alumina.

The catalyst preferably also contain 0.01% to 5%, preferably 0.1% to 3% by weight, with respect to the zeolite, of at least one metal from the group formed by elements from groups III and IV of the periodic table, i.e., selected from the group formed by germanium, tin, lead, boron, gallium, indium, thallium and silicon, preferably selected from the group formed by tin and indium.

The present invention also concerns a process for dismutation and/or transalkylation of toluene and/or alkylaromatic compounds containing at least 9 carbon atoms per molecule, preferably for dismutation of toluene to produce benzene and xylenes and/or transalkylation of toluene with AC9(+) compounds to produce xylenes from toluene-AC9(+) mixtures generally containing at most 50 mole % of AC9(+), the process being characterized in that the catalyst of the invention is used.

Any zeolite with a mordenite structure which is known to the skilled person is suitable for the present invention. Thus, for example, the zeolite used as a base to prepare the catalyst of the present invention is "large pore" mordenite in its sodium form, or "small pore" mordenite in its sodium form. When a commercially available zeolite is used which has the required specifications concerning the Si/Al ratio, at least one ion exchange step is generally carried out in at least one $NH_4NO_3$ solution to obtain a zeolite with a sodium content of less than 0.1%, preferably less then 0.05% by weight, and in its $NH_4^+$ form.

It is also possible to start from a mordenite with a molar Si/Al ratio which is lower and generally in the range 5 to the desired value. Thus at least one dealumination step will be required to reach the desired Si/Al molar ratio. Within this context, any dealurnination technique known to the skilled person can be used.

Using the operating method described in U.S. Pat. No. 4,780,436 in particular, calcining is carried out in a stream of dry air, then at least one ion exchange step using at least one $NH_4NO_3$ solution is carried out, to eliminate practically all of the alkaline cations, in particular sodium, present in the cationic position in the zeolite, then at least one framework dealumination cycle, steaming followed by an acid attack step, is carried out, comprising at least one cacining step carried out in the presence of steam, at a temperature which is generally in the range 550° C. to 850° C., followed by at least one acid attack step. The framework dealumination cycle, comprising at least one calcining step carried out on the mordenite in steam and at least one attack step carried out in an acid medium, can be repeated as many times as is necessary to obtain the desired characteristics. Similarly, after a calcining treatment carried out in steam, a number of successive acid attack steps, using different concentrations of acid solutions, can be carried out.

The mordenite can also be dealuminated by direct acid attack using all of the mineral or organic acids which are known to the skilled person. In the same manner as above, several acid attack steps may be necessary to achieve the desired Si/Al molar ratio. Mineral agents such as silica tetrachloride or ammonium hexafluorosilicate or organic agents such as the disodium salt of ethylenediaminetetraacetic acid can also produce the desired dealumination. Finally, this step can be carried out using dibasic carboxylic acids such as oxalic acid. Preferably, direct acid attack is carried out in a single step.

The zeolite which is at least partially in its acid form, with the high Si/Al molar ratio desired, must contain less than 0.1% by weight, preferably less than 0.05% by weight, of sodium.

It is possible to introduce the ions of at least one metal from the group formed by elements of groups VI, VII and VIII in an amount, expressed with respect to the zeolite, in the range 0.01% to 5%, preferably in the range 0.1% to 3% by weight. To produce a mordenite exchanged with transition metals selected from the group formed by elements from groups VI, VII and VIII, the sodium ions in the mordenite can be directly exchanged, but it is preferable to first exchange the sodium ions, preferably with $NH_4^+$ ions by allowing the solid to stand in an aqueous solution of an ammonium salt. The metals are then introduced either by ion exchange or by dry impregnation (no excess solution) or by impregnating using excess solution. If the desired catalyst is to include a number of these metals, these can be introduced either all in the same manner or each using different methods. For ion exchange, different metal cations can be introduced either simultaneously in a single or in a plurality of cation exchange operations using solutions containing a mixture of some or all of the cations, or successively in a series of exchanges using a single cation type.

The catalyst of the present invention optionally also contains at least one metal from the group formed by elements from groups III and IV.

The complement to 100% generally consists of the binder in the catalyst.

The binder (or matrix) comprised in the catalyst of the present invention is generally selected from elements of the group formed by clays, magnesia, aluminas, silicas, titanium oxide, boron oxide, zirconia, aluminium phosphates, titanium phosphates, zirconium phosphates and silica aluminas. Preferably, the binder is alumina.

The catalyst can be prepared using any method which is known to the skilled person. In general, a mixture of the matrix and the zeolite is formed, followed by forming. At least one element selected from the group formed by elements from groups VI, VII and VIII can be introduced either before forming, or during mixing, or into the zeolite itself before mixing or, as is preferable, after forming. Forming is generally followed by calcining, generally at a temperature in the range 250° C. to 600° C. At least one element from the group formed by groups VI, VII and VIII of the periodic table is introduced after this calcining step. In all cases, the elements are practically completely deposited on the zeolite, in a manner which is known to the skilled person, using deposit parameters, such as the nature of the precursor used to carry out the deposition. Optionally, at least one element from the group formed by elements from groups III and IV is added first.

The elements from the group formed by elements from groups VI, VII and VIII can also optionally be deposited on the zeolite-matrix mixture which has been formed by any process known to the skilled person. Such deposition is, for example, carried out using dry impregnation, excess impregnation or ion exchange.

Any precursor is suitable for deposition of these elements. As an example, in the case of ion exchange, from precursors based on platinum, palladium or nickel, platinum or palladium tetramine or nickel salts such as chlorides, nitrates, formates or acetates can be used.

Optionally, at least one other metal selected from the group formed by elements from groups III and IV are also introduced. All of the deposition techniques known to the skilled person and all of the precursors are suitable for introducing the supplementary metal.

When the catalyst contains several metals, these latter can be introduced either in the same manner or using different techniques, at any time during preparation before or after forming and in any order. In the case where the technique used is that of ion exchange, a plurality of successive exchange steps may be necessary to introduce the required quantities of metals.

One preferred method for preparing the catalyst of the invention consists of mixing the zeolite in a moist gel of matrix (generally obtained by mixing at least one acid and a powdered matrix), for example alumina, for the period necessary to obtain good homogeneity of the paste produced, namely for about ten minutes, for example, then passing the paste through a die to form extrudates, for example with a diameter in the range 0.4 mm to 4 mm. After oven drying for several minutes at 100° C. then calcining, for example for two hours at 400° C., at least one element, for example nickel, can be deposited, for example by ion exchange, deposition being followed by final calcining, for example for two hours at 400° C.

The catalyst of the invention is generally formed so that the catalyst is preferably obtained for subsequent use in the formed of pellets, aggregates, extrudates or spherules.

Preparation of the catalyst generally ends with final calcining, normally at a temperature which is in the range 250° C. to 600° C., preferably preceded by drying, for example oven drying, at a temperature which is in the range from ambient temperature to 250° C., preferably 40° C. to 200° C. The drying step is preferably carried out during the temperature rise required to carry out calcining.

The catalyst of the present invention is used in a process for dismutation of toluene to produce benzene and xylenes, and/or transalkylation of alkylaromatics, preferably toluene with AC9(+) compounds to produce xylenes, from toluene-AC9(+) mixtures generally containing at most 50 mole % of AC9(+) compounds. The process is generally carried out under the following operating conditions: a temperature in the range 250° C. to 600° C., preferably in the range 330° C. to 500° C.; a pressure in the range 10 to 60, preferably in the range 20 to 45 bar (1 bar=0.1 MPa); an hourly space velocity, expressed in kilograms of feed introduced per kilogram of catalyst per hour, in the range 0.1 to 10, preferably in the range 0.5 to 4; and a molar ratio of hydrogen to hydrocarbon(s) in the range 2 to 20, preferably in the range 3 to 12.

The following examples illustrate the invention without limiting its scope.

EXAMPLE 1

Preparation of Catalyst C1, not in Accordance with the Invention, Containing Mordenite and 0.6% by Weight of Nickel The starting zeolite was a Tosoh mordenite with an Si/Al ratio of 14.8 and a unit cell volume of 2.740 nm$^3$. The zeolite underwent ion exchange in a 10 N $NH_4NO_3$ solution at about 100° C. for 4 hours. The solid obtained contained 21 ppm of sodium.

This zeolite was then formed by extrusion with an alumina gel to obtain, after drying and calcining in dry air, a catalyst I1 which contained 80% by weight of mordenite zeolite in its H form and 20% of alumina.

This catalyst I1 was dry impregnated with a nickel nitrate solution to deposit 0.6% by weight of Ni on the catalyst. The moist solid was then dried at 120° C. for 12 hours and calcined in a stream of dry air at 500° C. for one hour. Catalyst C1 obtained contained 79.5% by weight of mordenite in its hydrogen form, 19.9% by weight of alumina and 0.61% by weight of nickel.

EXAMPLE 2

Preparation of Catalyst C2, in Accordance with the Invention

The starting material used was a mordenite zeolite, which had a global Si/Al atomic ratio of 7.6, and a sodium content, with respect to the weight of dry mordenite zeolite, of about 3.8% by weight.

This mordenite zeolite underwent acid attack, using an 8 N nitric acid solution at about 100° C. for 4 hours, to partially extract the aluminium atoms present in the zeolitic framework of the mordenite. The dealuminated mordenite zeolite then underwent ion exchange in a 10 N $NH_4NO_3$ solution at about 100° C. for 4 hours to extract the residual sodium.

After these treatments, the mordenite zeolite in its H form had a global Si/Al atomic ratio of 47.9, and a sodium content, with respect to the weight of dry mordenite zeolite, of 48 ppm by weight.

This zeolite was then formed by extrusion with an alumina gel to obtain, after drying and calcining in dry air, a catalyst I2 which contained 80% by weight of mordenite zeolite in its H form and 20% of alumina.

This catalyst I2 underwent dry impregnation with a nickel nitrate solution to deposit 0.6% by weight of Ni on the catalyst. The moist solid was dried at 120° C. for 12 hours then calcined in a stream of dry air at a temperature of 500° C. for one hour. Catalyst C2 obtained contained 79.5% of mordenite in its hydrogen form, 19.9% of alumina and 0.58% of nickel.

EXAMPLE 3

Preparation of Catalyst C3, in Accordance with the Invention, Containing Mordenite, 0.3% by Weight of Rhenium and 0.2% by Weight of Tin Catalyst I2 was first impregnated with an aqueous rhenium oxide solution to deposit 0.3% by weight of rhenium on the solid. Catalyst I3 was obtained. I3 then underwent to dry impregnation using a $Sn(Bu)_4$ solution in n-heptane to introduce 0.2% by weight of tin. Catalyst C3 obtained contained 79.6% by weight of mordenite, 19.9% of alumina, 0.32% of Re and 0.19% of Sn.

EXAMPLE 4

Evaluation of Catalytic Properties of Catalysts C1, C2 and C3 for Toluene Transformation The performances of catalysts C1, C2 and C3 were evaluated for toluene transformation to produce benzene and xylenes. The operating conditions were as follows:

temperature: 430° C;

pressure: 30 bar (1 bar=0.1 MPa);

hydrogen/toluene molar ratio: 4.

The catalysts were pretreated with a feed containing dimethyldisulphide (DNMDS) using a concentration such that the sulphur/metal atomic ratio was 1.5. This treatment was carried out over 3 hours at 400° C., keeping the hydrogen/hydrocarbon molar ratio at 4.

The stability of the catalysts over time was estimated by measuring the performances of the catalysts as a function of operating period. The conversion and benzene+xylenes selectivities were monitored under operating conditions which were kept constant over time. The results are shown in Tables 1 and 2 below.

TABLE 1

| Catalyst | Conversion after 5 days of operation (wt %) | Selectivity for benzene + xylenes (wt %) |
|---|---|---|
| C1 (not in accordance) | 47.1 | 88.3 |
| C2 (in accordance) | 48.9 | 88.7 |
| C3 (in accordance) | 49.2 | 88.6 |

TABLE 2

| Catalyst | Conversion after 14 days of operation (wt %) | Selectivity for benzene + xylenes (wt %) |
|---|---|---|
| C1 (not in accordance) | 40.8 | 88.8 |
| C2 in accordance | 46.9 | 89.1 |
| C3 in accordance | 46.7 | 89.2 |

The percentage deactivation represents the difference between the conversion at 14 days of operation and that at 5 days of operation, with respect to the conversion at 5 days of operation. It is shown in Table 3 below.

TABLE 3

| Catalyst | C1 (not in accordance) | C2 (in accordance) | C3 (in accordance) |
|---|---|---|---|
| Percentage deactivation | 13.4 | 4.0 | 5.1 |

It can be seen that catalysts C2 and C3 of the invention are more active than comparative catalyst C1.

Further, catalyst C1, not in accordance with the invention, was deactivated by 13.4%, while catalysts C2 and C3 were only deactivated by 4.0% and 5.1% respectively over the same period. Catalysts C2 and C3 of the invention thus have a substantially improved stability over time with respect to comparative catalyst C1.

We claim:

1. A final calcined catalyst for dismutation and/or transalkylation of toluene and/or alkylaromatics containing at least 9 carbon atoms per molecule which contains:
    40% to 90% by weight of at least one zeolite with a mordenite structure which is at least partially in its acid form, having a Si/Al molar ratio of 47.9 to 60, said mordenite containing at most 0.1% by weight (expressed with respect to zeolite) of sodium;
    a total of 0.01% to 5% weight, with respect to the zeolite, of at least one metal from the group formed by elements from groups VI, VII and VIII of the periodic table;
    10% to 60% by weight of at least one binder.
2. A catalyst according to claim 1, comprising 75% to 85% by weight of zeolite and 15% to 25% by weight of binder.
3. A catalyst according to claim 1, in which the Si/Al molar ratio of the zeolite is in the range 40 to 60.
4. A catalyst according to claim 1, in which the binder is selected from elements of the group consisting of clays, magnesia, aluminas, silicas, titanium oxide, boron oxide, zirconia, aluminium phosphates, titanium phosphates, zirconium phosphates and silica aluminas.
5. A catalyst according to claim 1, in which said metal is selected from the group consisting of palladium, platinum, rhenium and nickel.
6. A catalyst according to claim 1, in which it further comprises a total of 0.01% to 5% by weight, with respect to the zeolite, of at least one metal selected from the group consisting of elements from groups III and IV of the periodic table.
7. A catalyst according to claim 6, in which said metal is tin or indium.
8. A catalyst according to claim 1, wherein the content of said at least one metal from the group formed by elements from groups VI, VII and VIII of the periodic table is 0.1% to 3.0%.
9. A catalyst according to claim 1, having the upper limit of the Si/Al molar ratio is not higher than 55.
10. A catalyst according to claim 9, wherein the content of said at least one metal from the group formed by elements from groups VI, VII and VIII of the periodic table is 0.1% to 3.0%.
11. A catalyst according to claim 1, wherein the catalyst is devoid of elements of group VI of the periodic table.
12. A process for comprising reacting toluene under dismutation conditions in the presence of the catalyst according to claim 1, so as to produce xylenes and benzene.
13. A process comprising reacting a starting material comprising toluene under transalkylation conditions with alkyl aromatic compounds containing at least 9 carbon atoms per molecule, in contact with a catalyst according to claim 1, so as to produce xylenes.
14. A process according to claim 13, wherein the starting material comprises a mixture of toluene and alkyl aromatic compounds containing at least 9 carbon atoms wherein the mixture contains at most 50 mole percent of the alkyl aromatic compounds containing at least 9 carbon atoms.
15. A process according to claim 14, carried out under the following operating conditions: a temperature in the range 250° C. to 600° C.; a pressure in the range 1 to 6 MPa; an hourly space velocity, expressed in kilograms of feed introduced per kilogram of catalyst per hour, in the range 0.1 to 10; and a hydrogen to hydrocarbon(s) molar ratio which is in the range 2 to 20.
16. A process according to claim 13, carried out under the following operating conditions: a temperature in the range 250° C. to 600° C.; a pressure in the range 1 to 6 MPa; an hourly space velocity, expressed in kilograms of feed introduced per kilogram of catalyst per hour, in the range 0.1 to 10; and a hydrogen to hydrocarbon(s) molar ratio which is in the range 2 to 20.
17. A process for comprising reacting toluene under dismutation conditions in the presence of the catalyst according to claim 2 so as to produce xylenes and benzene.
18. A process comprising reacting a starting material comprising toluene under transalkylation conditions with alkyl aromatic compounds containing at least 9 carbon atoms per molecule, in contact with a catalyst according to claim 2 so as to produce xylenes.
19. A process according to claim 2, wherein the starting material comprises a mixture of toluene and alkyl aromatic compounds containing at least 9 carbon atoms wherein the mixture contains at most 50 mole percent of the alkyl aromatic compounds containing at least 9 carbon atoms.
20. A process for comprising reacting toluene under dismutation conditions in the presence of the catalyst according to claim 6 so as to produce xylenes and benzene.
21. A process comprising reacting a starting material comprising toluene under transalkylation conditions with alkyl aromatic compounds containing at least 9 carbon atoms per molecule, in contact with a catalyst according to claim 6 so as to produce xylenes.
22. A process according to claim 6, wherein the starting material comprises a mixture of toluene and alkyl aromatic compounds containing at least 9 carbon atoms wherein the mixture contains at most 50 mole percent of the alkyl aromatic compounds containing at least 9 carbon atoms.

* * * * *